(12) United States Patent
Gallou et al.

(10) Patent No.: US 7,189,844 B2
(45) Date of Patent: Mar. 13, 2007

(54) RING-CLOSING METATHESIS PROCESS IN SUPERCRITICAL FLUID

(75) Inventors: Fabrice Gallou, Danbury, CT (US); Nathan Yee, Danbury, CT (US)

(73) Assignee: Boehringer Ingelheim International GmbH, Ingelheim (DE)

( * ) Notice: Subject to any disclaimer, the term of this patent is extended or adjusted under 35 U.S.C. 154(b) by 20 days.

(21) Appl. No.: 11/222,882

(22) Filed: Sep. 9, 2005

(65) Prior Publication Data

US 2006/0063915 A1   Mar. 23, 2006

Related U.S. Application Data

(60) Provisional application No. 60/610,685, filed on Sep. 17, 2004.

(51) Int. Cl.
*C07D 245/00* (2006.01)
(52) U.S. Cl. .................................................. 540/460
(58) Field of Classification Search ................ 540/460
See application file for complete search history.

(56) References Cited

U.S. PATENT DOCUMENTS

| 6,608,027 | B1 | 8/2003 | Tsantrizos et al. |
| 2003/0181363 | A1 | 9/2003 | Llinas-Brunet et al. |
| 2003/0224977 | A1 | 12/2003 | Llinas-Brunet et al. |
| 2004/0248779 | A1 | 12/2004 | Dersch et al. |
| 2005/0049187 | A1 | 3/2005 | Brandenburg et al. |
| 2005/0075279 | A1 | 4/2005 | Llinas-Brunet et al. |
| 2005/0080005 | A1 | 4/2005 | Llinas Brunet et al. |
| 2005/0154186 | A1 | 7/2005 | Gallou et al. |

FOREIGN PATENT DOCUMENTS

| WO | WO 00/59929 | 10/2000 |
| WO | WO 03/064455 A2 | 8/2003 |
| WO | WO 2005/028501 A1 | 3/2005 |
| WO | WO 2005/056182 A1 | 6/2005 |
| WO | WO 2005/090383 A2 | 9/2005 |

OTHER PUBLICATIONS

Alois Furstner, et al, Olefin Metathesis in Supercritical Carbon Dioxide, J. Am. Chem. Soc. 2001, 123, 9000-9006.

*Primary Examiner*—Bruck Kifle
(74) *Attorney, Agent, or Firm*—Michael P. Morris; Mary-Ellen M. Devlin; Philip I. Datlow

(57) ABSTRACT

Disclosed is a process for preparing a compound of formula I comprising cyclizing a diene compound of formula III in the presence of a ruthenium catalyst in a suitable organic solvent, wherein the process is performed in a gaseous fluid at supercritical or near-supercritical conditions:

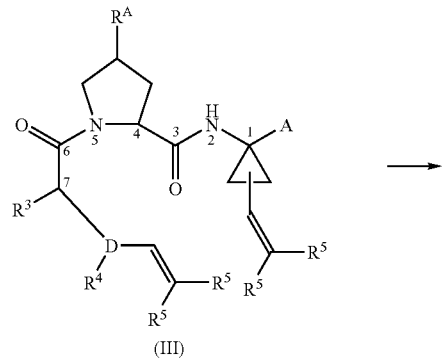

(III)

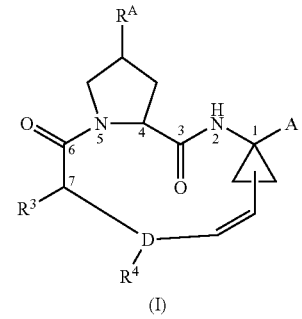

(I)

The compounds of formula (I) are active agents for the treatment of hepatitis C viral (HCV) infections or are intermediates useful for the preparation of anti-HCV agents.

18 Claims, No Drawings

RING-CLOSING METATHESIS PROCESS IN SUPERCRITICAL FLUID

CROSS-REFERENCE TO RELATED APPLICATIONS

This application claims the benefit of U.S. Provisional Application No. 60/610,685, filed Sep. 17, 2004.

BACKGROUND OF THE INVENTION

1. Technical Field

The invention relates to an improved process for the preparation of certain macrocyclic compounds useful as agents for the treatment of hepatitis C viral (HCV) infections. More specifically, the invention relates to an improved process for the preparation of such macrocyclic compounds via a ring closing metathesis ("RCM") reaction in a gaseous fluid at supercritical or near-supercritical conditions.

2. Background Information

The macrocyclic compounds of the following formula (I) and methods for their preparation are known from: Tsantrizos et al., U.S. Pat. No. 6,608,027 B1; Llinas Brunet et al, U.S. Application Publication No. 2003/0224977 A1; Llinas Brunet et al, U.S. Application Publication No. 2005/0075279 A1; Llinas Brunet et al, U.S. Application Publication No. 2005/0080005 A1 Brandenburg et al., U.S. Application Publication No. 2005/0049187 and Samstag et al., U.S. Application Publication No. 2004/0248779 A1, :

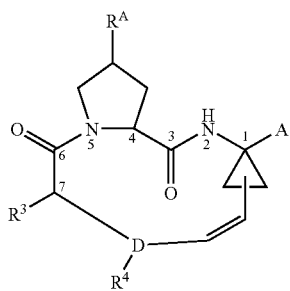

(I)

wherein
$R^A$ is a leaving group or a group of formula II

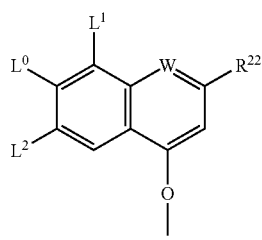

(II)

W is CH or N,
$L^0$ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^{23})_2$,
wherein each $R^{23}$ is independently H, $C_{1-6}$ alkyl or $C_{3-6}$ cycloalkyl;
$L^1$, $L^2$ are each independently H, halogen, $C_{1-4}$alkyl, —O—$C_{1-4}$alkyl, or —S—$C_{1-4}$alkyl (the sulfur being in any oxidized state); or
$L^0$ and $L^1$ or
$L^0$ and $L^2$ may be covalently bonded to form together with the two C-atoms to which they are linked a 4-, 5- or 6-membered carbocyclic ring wherein one or two (in the case of a 5- or 6-membered ring) —$CH_2$— groups not being directly bonded to each other, may be replaced each independently by —O— or $NR^a$ wherein $R^a$ is H or $C_{1-4}$alkyl, and wherein said ring is optionally mono- or di-substituted with $C_{1-4}$ alkyl;
$R^{22}$ is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxyalkyl, $C_{3-6}$ cycloalkyl, $C_{6\ or}\ C_{10}$ aryl or Het, wherein Het is a five-, six-, or seven-membered saturated or unsaturated heterocycle containing from one to four heteroatoms selected from nitrogen, oxygen and sulfur;
said cycloalkyl, aryl or Het being substituted with $R^{24}$,
wherein $R^{24}$ is H, halo, $C_{1-6}$ alkyl, $C_{3-6}$ cycloalkyl, $C_{1-6}$ alkoxy, $C_{3-6}$ cycloalkoxy, $NO_2$, $N(R^{25})_2$, NH—C(O)—$R^{25}$; or NH—C(O)—NH—$R^{25}$, wherein each $R^{25}$ is independently: H, $C_{1-6}$ alkyl or $C_{3-6}$ cycloalkyl;
or $R^{24}$ is NH—C(O)—$OR^{26}$ wherein $R^{26}$ is $C_{1-6}$ alkyl or $C_{3-6}$ cycloalkyl;
$R^3$ is hydroxy, $NH_2$, or a group of formula —NH—$R^9$, wherein $R^9$ is $C_{6\ or\ 10}$ aryl, heteroaryl, —C(O)—$R^{20}$, —C(O)—NHR$^{20}$ or —C(O)—$OR^{20}$, wherein $R^{20}$ is $C_{1-6}$ alkyl or $C_{3-6}$ cycloalkyl;
D is a 3 to 7 atom saturated alkylene chain optionally containing one to three heteroatoms independently selected from: O, S or N—$R^{27}$, wherein $R^{27}$ is H, $C_{1-6}$alkyl, $C_{3-6}$cycloalkyl or C(O)$R^{28}$, wherein $R^{28}$ is $C_{1-6}$alkyl, $C_{3-6}$cycloalkyl or $C_{6\ or\ 10}$ aryl;
$R^4$ is H, or from one to three substituents at any carbon atom of said chain D, said substituent independently selected from the group consisting of: $C_{1-6}$ alkyl, $C_{1-6}$ haloalkyl, $C_{1-6}$ alkoxy, hydroxy, halo, amino, oxo, thio, or $C_{1-6}$ thioalkyl; and
A is an amide of formula —C(O)—NH—$R^{11}$, wherein $R^{11}$ is selected from the group consisting of: $C_{1-8}$ alkyl, $C_{3-6}$ cycloalkyl, $C_{6\ or\ 10}$ aryl, $C_{7-16}$ aralkyl, or $SO_2R^{5A}$ wherein $R^{5A}$ is $C_{1-8}$ alkyl, $C_{3-7}$ cycloalkyl,$C_{1-6}$ alkyl-$C_{3-7}$ cycloalkyl;
or A is a carboxylic acid or a pharmaceutically acceptable salt or ester thereof.

The compounds of formula (I) are disclosed in the above-mentioned patent documents as being active agents for the treatment of hepatitis C viral (HCV) infections, or as intermediates useful for the preparation of such anti-HCV agents as described therein, and are prepared therein via ring-closing metathesis of an acyclic diolefin using ruthenium-based catalysts in a suitable organic solvent.

It has been reported that supercritical carbon dioxide may be used as a versatile reaction medium for conducting certain olefin metathesis reactions, and in the case of ring-closing olefin metathesis reactions, the solubility properties of the supercritical carbon dioxide may be exploited to isolate the low molecular weight RCM products from the ruthenium complex via selective supercritical fluid extraction (Furstner et al., *J. Am. Chem. Soc.*, 2001, 123(37), 9000; W. Leitner, *C. R. Acad. Sci. Paris, Serie IIc, Chimie*, 2000, 3, 595; Furstner et al., *Angew. Chem.*, 1997, 109, 2562, and *Angew. Chem. Int. Ed. Engl.*, 1997, 36, 2466; and Pandey et. al., *J. Phys. Chem. B.* 2002, 106(7), 1820). However, although numerous examples are provided using lower molecular weight RCM products, there is no disclosure or suggestion that such technique would be effective for higher molecular weight RCM products, such as the macrocyclic compounds of formula (I).

BRIEF SUMMARY OF THE INVENTION

Surprisingly, supercritical or near-supercritical fluids have been found useful as an optimal reaction medium for conducting the ring closing metathesis of the diolefins leading to the macrocyclic compounds of formula I. Accordingly, the present invention is directed to a process for preparing a compound of formula I as previously set forth, said process comprising cyclizing a diene compound of the following formula III in the presence of a ruthenium catalyst in a suitable organic solvent, wherein the process is performed in a gaseous fluid at supercritical or near-supercritical conditions to obtain a compound of the following formula I:

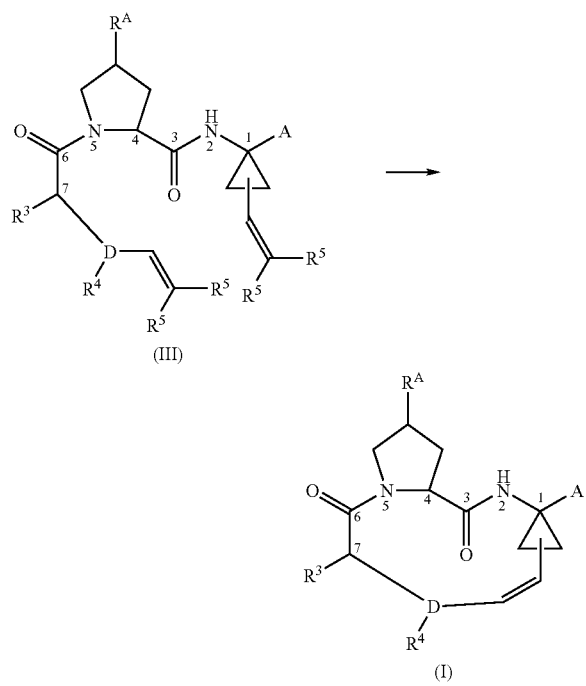

wherein the variable groups $R^A$, $R^3$, $R^4$, D and A are as defined previously and each $R^5$ in formula III is independently selected from H, $C_{1-6}$alkyl and $C_{3-6}$cycloalkyl.

DETAILED DESCRIPTION OF THE INVENTION

Definitions

Terms not specifically defined herein should be given the meanings that would be given to them by one of ordinary skill in the art in light of the disclosure and the context. As used in the present specification, however, unless specified to the contrary, the following terms have the meaning indicated and the following conventions are adhered to.

In the groups, radicals, or moieties defined below, the number of carbon atoms is often specified preceding the group, for example, $C_{1-6}$ alkyl means an alkyl group or radical having 1 to 6 carbon atoms. In general, for groups comprising two or more subgroups, the last named group is the radical attachment point, for example, "thioalkyl" means a monovalent radical of the formula HS-Alk-. Unless otherwise specified below, conventional definitions of terms control and conventional stable atom valences are presumed and achieved in all formulas and groups.

The term "$C_{1-x}$ alkyl" as used herein, either alone or in combination with another substituent, means acyclic, straight or branched chain alkyl substituents containing the specified 1 to x number of carbon atoms.

The term "$C_{1-x}$ alkoxy" as used herein, either alone or in combination with another substituent, means the substituent $C_{1-x}$ alkyl-O— wherein alkyl is as defined above containing up to x carbon atoms.

The term "saturated alkylene chain" as used herein means a divalent alkyl substituent derived by the removal of one hydrogen atom from each end of a saturated straight or branched chain aliphatic hydrocarbon and includes, for example,

The term "$C_{3-x}$ cycloalkoxy" as used herein, either alone or in combination with another substituent, means the substituent $C_{3-x}$ cycloalkyl-O— containing from 3 to x carbon atoms.

The term "$C_6$ or $C_{10}$ aryl" as used herein, either alone or in combination with another substituent, means either an aromatic monocyclic system containing 6 carbon atoms or an aromatic bicyclic system containing 10 carbon atoms. For example, aryl includes a phenyl or a naphthyl ring system.

The term "$C_{7-16}$ aralkyl" as used herein, either alone or in combination with another substituent, means an aryl as defined above linked through an alkyl group, wherein alkyl is as defined above containing from 1 to 6 carbon atoms. Aralkyl includes for example benzyl, and butylphenyl.

The term "Het" as used herein, either alone or in combination with another substituent, means a monovalent substituent derived by removal of a hydrogen from a five-, six-, or seven-membered saturated or unsaturated (including aromatic) heterocycle containing carbon atoms and from one to four ring heteroatoms selected from nitrogen, oxygen and sulfur. Examples of suitable heterocycles include: tetrahydrofuran, thiophene, diazepine, isoxazole, piperidine, dioxane, morpholine, pyrimidine or

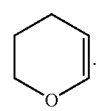

The term "Het" also includes a heterocycle as defined above fused to one or more other cycle be it a heterocycle or a carbocycle, each of which may be saturated or unsaturated. One such example includes thiazolo[4,5-b]-pyridine. Although generally covered under the term "Het", the term "heteroaryl" as used herein precisely defines an unsaturated heterocycle for which the double bonds form an aromatic system. Suitable example of heteroaromatic "heteroaryl" systems include: quinoline, indole, pyridine,

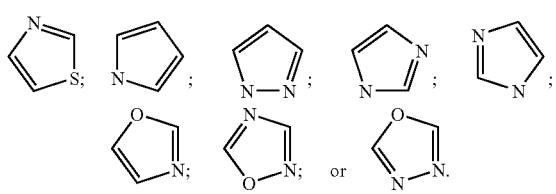

The term "oxo" means the double-bonded group (═O) attached as a substituent.

The term "thio" means the double-bonded group (=S) attached as a substituent.

In general, all tautomeric forms and isomeric forms and mixtures, whether individual geometric isomers, stereoisomers, optical isomers or racemic or non-racemic mixtures of isomers, of a chemical structure or compound are intended, unless the specific stereochemistry or isomeric form is specifically indicated in the compound name or structure.

The term "pharmaceutically acceptable ester" as used herein, either alone or in combination with another substituent, means esters of the compound of formula I in which any of the carboxylic acid functions of the molecule, but preferably the carboxy terminus, is replaced by an alkoxycarbonyl function:

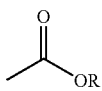

in which the R moiety of the ester is selected from alkyl (e.g. methyl, ethyl, n-propyl, t-butyl, n-butyl); alkoxyalkyl (e.g. methoxymethyl); alkoxyacyl (e.g. acetoxymethyl); aralkyl (e.g. benzyl); aryloxyalkyl (e.g. phenoxymethyl); aryl (e.g. phenyl), optionally substituted with halogen, $C_{1-4}$ alkyl or $C_{1-4}$ alkoxy. Other suitable prodrug esters are found in *Design of Prodrugs*, Bundgaard, H. Ed. Elsevier (1985) incorporated herewith by reference. Such pharmaceutically acceptable esters are usually hydrolyzed in vivo when injected in a mammal and transformed into the acid form of the compound of formula I. With regard to the esters described above, unless otherwise specified, any alkyl moiety present advantageously contains 1 to 16 carbon atoms, particularly 1 to 6 carbon atoms. Any aryl moiety present in such esters advantageously comprises a phenyl group. In particular the esters may be a $C_{1-16}$ alkyl ester, an unsubstituted benzyl ester or a benzyl ester substituted with at least one halogen, $C_{1-6}$ alkyl, $C_{1-6}$ alkoxy, nitro or trifluoromethyl.

The term "pharmaceutically acceptable salt" as used herein includes those derived from pharmaceutically acceptable bases. Examples of suitable bases include choline, ethanolamine and ethylenediamine. $Na^+$, $K^+$, and $Ca^{++}$ salts are also contemplated to be within the scope of the invention (also see *Pharmaceutical Salts*, Birge, S. M. et al., J. Pharm. Sci., (1977), 66, 1–19, incorporated herein by reference).

By the term "about" with respect to a recited value is meant ±20% of the recited value, preferably ±10%, more preferably ±5%, even more preferably ±1%. When the term "about" is used in relation to a range of values, the term "about" is intended to qualify each recited end-point of the range. For example, the phrase "about 70 to 80° C." is equivalent to "about 70 to about 80° C.".

By "gaseous fluid", or "supercritical fluid" is meant (1) a fluid or mixture of fluids that is gaseous under atmospheric conditions and that has a moderate critical temperature (i.e., ≦200° C.), or (2) a fluid that has previously found use as a supercritical fluid. Examples of gaseous fluids include those that have a critical temperature of less than about 200° C. and a critical pressure of less than about 689 bar. Specific examples include carbon dioxide, nitrous oxide, trifluoromethane, ethane, ethylene, propane, sulfur hexafluoride, propylene, butane, isobutane, pentane, and mixtures thereof.

Embodiments of the Invention

In the synthetic schemes below, unless specified otherwise, all the substituent groups in the chemical formulas shall have the same meanings as in the Formula (I). The reactants used in the synthetic schemes described below, including the diene compounds of formula III, may be obtained either as described herein, or if not described herein, are themselves either commercially available or may be prepared from commercially available materials by methods known in the art. Certain starting materials, for example, may be obtained by methods described in the International Patent Applications WO 00/59929, WO 00/09543 and WO 00/09558, U.S. Pat. No. 6,323,180 B1, U.S. Pat. No. 6,608, 027 B1 and U.S. Application Publication No. 2003/0224977 A1.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by High Pressure Liquid Chromatography (HPLC), if desired, and intermediates and products may be purified by chromatography on silica gel and/or by recrystallization.

In one general embodiment, the present invention is directed to a process for preparing a compound of formula I, said process comprising cyclizing a diene compound of the following formula III in the presence of a ruthenium catalyst in a suitable organic solvent, wherein the process is performed in a gaseous fluid at supercritical or near-supercritical conditions to obtain a compound of the following formula I:

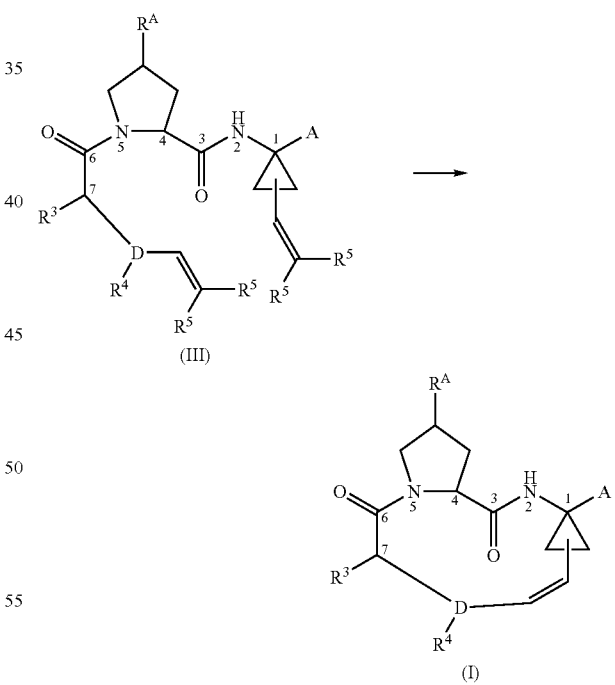

wherein the variable groups $R^A$, $R^3$, $R^4$, D and A are as defined previously and each $R^5$ in formula III is independently selected from H, $C_{1-6}$-alkyl and $C_{3-6}$cycloalkyl.

The gaseous fluid employed in the inventive method includes, for example, any gaseous fluid that is commonly employed in conventional supercritical fluid processes. Examples of gaseous fluids that may be used include those that have a critical temperature of less than about 200° C. and a critical pressure of less than about 689 bar. Specific examples include carbon dioxide, nitrous oxide, trifluoromethane, ethane, ethylene, propane, sulfur hexafluoride, propylene, butane, isobutane, pentane, and mixtures thereof. A preferred gaseous fluid is carbon dioxide.

Preferred supercritical or near-supercritical process conditions for the reaction step are as follows: The reaction is preferably conducted at a temperature in the range of about 0.8 to 3.0 times the critical temperature of the gaseous fluid in degrees Kelvin, and at a pressure in the range of about 0.5 to 30 times the critical pressure of the gaseous fluid; more preferably at a temperature in the range of about 2.0 to 3.0 times the critical temperature of the gaseous fluid in degrees Kelvin, and at a pressure in the range of about 1 to 10 times the critical pressure of the gaseous fluid.

The type and amount of gaseous fluid and the processing conditions to be employed in any particular case can be readily determined by a person skilled in field of supercritical fluid processing techniques with reference to the description and examples set forth herein and known techniques. In a specific embodiment, the gaseous fluid is carbon dioxide and the reaction step is conducted at a temperature of about 70 to 80° C. and at a pressure of about 95 to 238 bar.

The organic solvent that may be used is any suitable organic solvent in which the compound of formula (III) is substantially soluble and which, itself, is substantially soluble in the gaseous fluid under selected processing conditions. Examples of organic solvents that may be used include toluene, dichloromethane, THF, dioxane, ethyl acetate, tert-butyl acetate, methyl-tert-butyl ether, methanol, water, and mixtures thereof.

Suitable ruthenium catalysts for the metathesis cyclization step include any of the well-known ruthenium catalysts useful for RCM reactions, including the compounds of formula A, B, C, D or E:

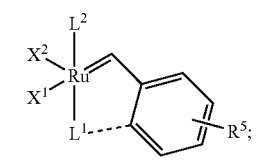

(A)

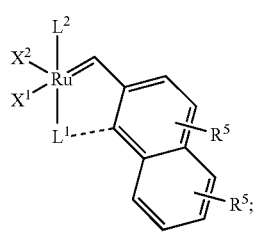

(B)

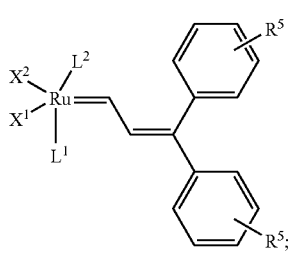

(C)

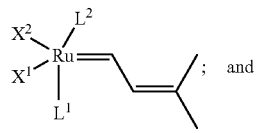

(D)

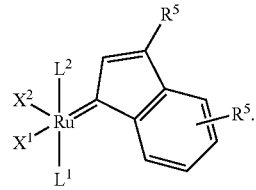

(E)

wherein
$X^1$ and $X^2$ each independently represent an anionic ligand,
$L^1$ represents a neutral electron donor ligand which is bonded to the ruthenium atom and is optionally bonded to the phenyl group, and
$L^2$ represents a neutral electron donor ligand which is bonded to the ruthenium atom;
and $R^5$ is selected from one or more substituents on the benzene ring, each substituent independently selected from hydrogen, $C_{1-6}$alkyl, halo$C_{1-6}$alkyl, HS—$C_{1-6}$alkyl, HO—$C_{1-6}$alkyl, perfluoro$C_{1-6}$alkyl, $C_{3-6}$ cycloalkyl, $C_{1-6}$alkoxy, hydroxyl, halogen, nitro, imino, oxo, thio or aryl; and
wherein $X^2$ and $L^2$ may optionally together-form a chelating bidentate ligand.

In another embodiment the ruthenium catalyst is selected from A-1 and A-2:

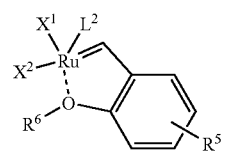

(A-1)

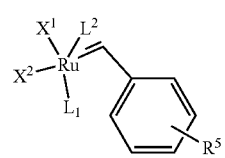

(A-2)

wherein:
$L^1$ is a trisubstituted phosphine group of the formula $PR_3$, wherein R is selected from $C_{1-6}$alkyl and $C_{3-8}$cycloalkyl,
$L^2$ is a trisubstituted phosphine group of the formula $PR_3$, wherein R is selected from $C_{1-6}$alkyl and $C_{3-8}$cycloalkyl, or $L^2$ is a group of the formula A or B:

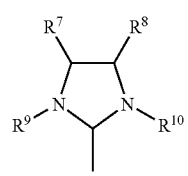

(A)

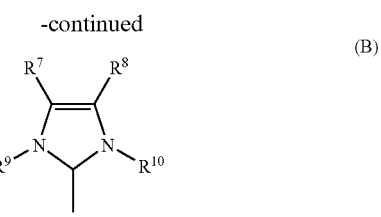

wherein

R[7] and R[8] each independently represent a hydrogen atom or a $C_{1-6}$ alkyl, $C_{2-6}$ alkenyl, $C_{6-12}$ aryl or $C_{6-12}$ aryl-$C_{1-6}$ alkyl group; and R[9] and R[10] each independently represent a hydrogen atom or a $C_{1-6}$ alkyl, $C_{2-6}$ alkenyl, $C_{6-12}$ aryl or $C_{6-12}$ aryl-$C_{1-6}$ alkyl group, each optionally substituted by one, two or three groups selected from hydrogen, $C_{1-6}$alkyl, halo$C_{1-6}$alkyl, HS—$C_{1-6}$alkyl, HO—$C_{1-6}$alkyl, perfluoro$C_{1-6}$alkyl, $C_{3-6}$ cycloalkyl, $C_{1-6}$alkoxy, hydroxyl, halogen, nitro, imino, oxo, thio or aryl;

X[1] and X[2] each independently represent a halogen atom;

R[5] represent hydrogen or nitro; and

R[6] represents a $C_{1-6}$ alkyl group.

In another embodiment the ruthenium catalyst is selected from:

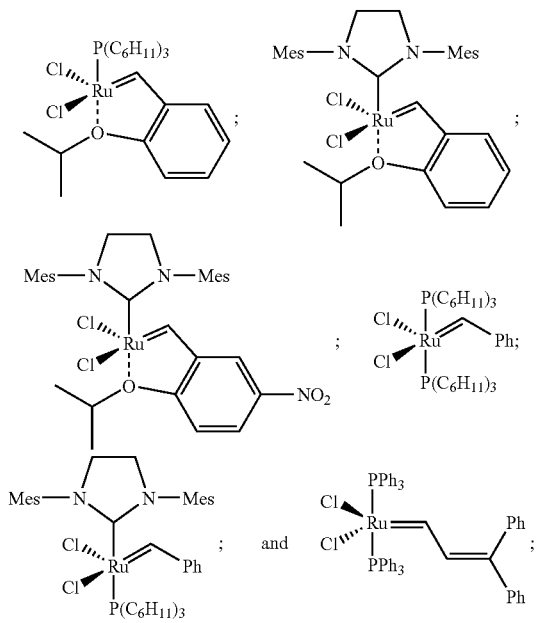

where Ph is phenyl and Mes is 2,4,6-trimethylphenyl.

Ruthenium-based catalysts useful for the metathesis cyclization step, such as those set forth above, are all known catalysts that may be obtained by known synthetic techniques. For example, see the references cited in the Background section above as well as the following references for examples of such ruthenium-based catalysts:

Organometallics 2002, 21, 671; 1999, 18, 5416; and 1998, 17, 2758;

J. Am. Chem. Soc. 2001, 123, 6543; 1999, 121, 791; 1999, 121, 2674; 2002, 124, 4954; 1998, 120, 2484; 1997, 119, 3887; 1996, 118, 100; and 1996, 118, 9606

J. Org. Chem. 1998, 63, 9904; and 1999, 64, 7202;

Angew. Chem. Int. Ed. Engl. 1998, 37, 2685; 1995, 34, 2038; 2000, 39, 3012 and 2002, 41, 4038;

U.S. Pat. Nos. 5,811,515; 6,306,987 B1; and 6,608,027 B1

The relative concentration levels of the starting material of formula III and the catalyst, as well as the other processing conditions, can be readily adjusted by a person skilled in the art to obtain optimum results for any particular process. In one particular embodiment, the starting material compound of formula III is present in the reaction mixture at a concentration of about 0.007 M to 0.014 M and the catalyst is present in the reaction mixture at a concentration of about 25 to 50 mol % relative to the compound of formula III. In another embodiment, the compound of formula III is present in the reaction mixture at a concentration of about 0.01 M and the catalyst is present in the reaction mixture at a concentration of about 25 mol % relative to the compound of formula III.

The process conditions for any specific process within the scope of the present invention can be readily selected and adjusted by one skilled in the art to obtain optimized results, i.e. increased product yields and decreased by-products. In one embodiment, the process of the present invention results in a yield of formula I product of at least about 65% and less than about 10% dimeric by-products. Another embodiment is where the process of the present invention results in a yield of formula I product of at least about 75% and less than about 5% dimeric by-products.

Wide variability is possible within the scope of the process of the present invention. For example, the diene compound of formula III in an organic solvent and the catalyst may be added into a reaction vessel in such a way that they are kept physically separated, and thus non-reactive, prior to pressurization of the reaction vessel with the gaseous fluid at which point the reaction takes place. Alternatively, a reaction vessel containing the compound of formula III in an organic solvent may be pressurized with a gaseous fluid to supercritical or near supercritical conditions, and then the catalyst is added to the vessel at which point the reaction takes place. Other variations are possible within the scope of the invention and all such variations are covered by the present invention if the RCM reaction takes place in a gaseous fluid at supercritical or near-supercritical conditions to obtain the cyclized product of formula I.

At the conclusion of the reaction, the gaseous fluid may be vented from the system and the macrocyclic product of formula I can be separated from the reaction mixture using conventional techniques. For example, some or all of the ruthenium metal may be removed from the reaction mixture by treatment with a suitable heavy metal scavenger, such as trishydroxymethylphosphine (THP) or other agents known to scavenge heavy metals. The reaction mixture is washed with water, followed by partial concentration of the organic solution (e.g., by distillation process). The organic solution may be decolorized, such as by the addition of activated charcoal with subsequent filtration, and then is added to a suitable solvent at a suitable temperature, such as pre-cooled methylcyclohexane, which causes precipitation of the product compound of formula (I) that is collected by filtration.

Additional Embodiments of the Invention

In a specific embodiment of the process, a compound of formula I is prepared wherein:

R[4] is a leaving group selected from: OH, O-PG, where PG is a protecting group, or —$OSO_2$—R[27], wherein R[27] is selected from p-tolyl, p-bromophenyl, p-nitrophenyl, methyl, trifluoromethyl, perfluorobutyl and 2,2,2-trifluoroethyl;

or $R^4$ is a group of formula II, and

W is N;

$L^0$ is H, $C_{1-6}$ alkyl, $C_{1-6}$ alkoxy, hydroxy, chloro;

$L^1$ and $L^2$ are each independently H, halogen or $C_{1-4}$alkyl;

$R^{22}$ is H, $C_{1-6}$ thioalkyl, $C_{1-6}$ alkoxy, phenyl or Het selected from the group consisting of:

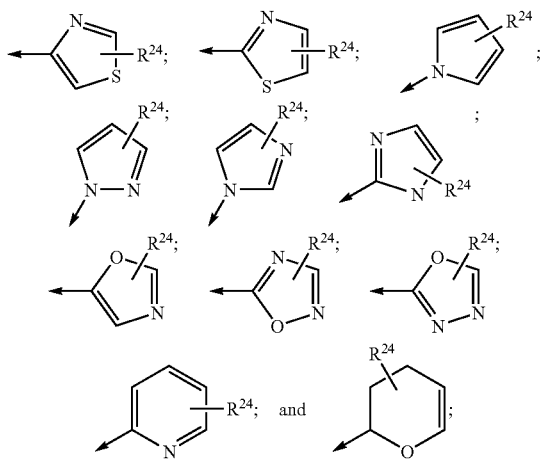

wherein $R^{24}$ is H, $C_{1-6}$ alkyl, NH—$R^{25}$, NH—$C(O)$—$R^{25}$; NH—$C(O)$—NH—$R^{25}$, wherein each $R^{25}$ is independently: H, $C_{1-6}$ alkyl, or $C_{3-6}$ cycloalkyl; or NH—$C(O)$—$OR^{26}$, wherein $R^{26}$ is $C_{1-6}$ alkyl; or $R^3$ is NH—$C(O)$—$OR^{20}$, wherein $R^{20}$ is $C_{1-6}$ alkyl, or $C_{3-6}$ cycloalkyl;

D is a 4 to 6 atom saturated alkylene chain optionally containing one or two heteroatoms independently selected from: O, S or N—$R^{27}$, wherein $R^{27}$ is H, $C_{1-6}$alkyl or $C_{2-7}$acyl;

$R^4$ is H or $C_{1-6}$ alkyl;

and A is a carboxylic acid or a pharmaceutically acceptable salt or ester thereof.

In another specific embodiment of the process, a compound of formula I is prepared wherein:

$R^A$ is a leaving group selected from: OH and —$OSO_2$—$R^{27}$, wherein $R^{27}$ is selected from p-tolyl, p-bromophenyl, p-nitrophenyl, methyl, trifluoromethyl, perfluorobutyl and 2,2,2-trifluoroethyl;

$R^3$ is NH—$C(O)$—$OR^{20}$, wherein $R^{20}$ is butyl, cyclobutyl or cyclopentyl;

$R^4$ is H or $C_{1-6}$ alkyl;

D is a 5 atom saturated alkylene chain; and

A is a carboxylic acid or a pharmaceutically acceptable salt or ester thereof.

In another specific embodiment of the process, a compound of formula I is prepared wherein:

$R^A$ is —$OSO_2$—$R^{27}$, wherein $R^{27}$ is p-bromophenyl;

$R^3$ is NH—$C(O)$—$OR^{20}$, wherein $R^{20}$ is cyclopentyl;

$R^4$ is H;

D is a 5 atom all carbon chain containing one cis double bond at position 13,14; and the right-hand portion of formula (I) is a moiety of the following formula wherein the position 14-cyclopropyl bond is syn to the ester group:

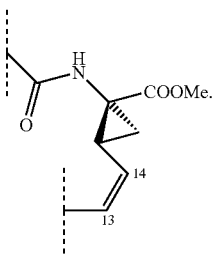

In another specific embodiment of the process:
(a) the gaseous fluid is carbon dioxide and the process is performed at a temperature in the range of about 70 to 80° C. and a pressure in the range of about 95 to 238 bar.
(b) the ruthenium catalyst is selected from:

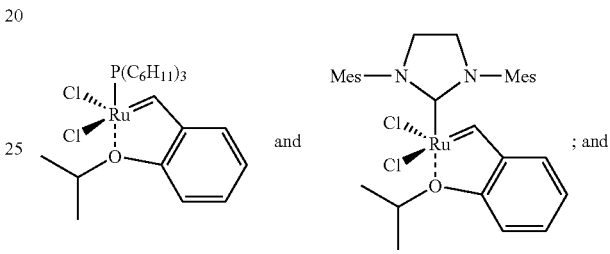

(c) in the compounds of formula (1) and (III):

$R^A$ is a leaving group selected from: OH and —$OSO_2$—$R^{27}$, wherein $R^{27}$ is selected from p-tolyl, p-bromophenyl, p-nitrophenyl, methyl, trifluoromethyl, perfluorobutyl and 2,2,2-trifluoroethyl;

$R^3$ is NH—$C(O)$—$OR^{20}$, wherein $R^{20}$ is butyl, cyclobutyl or cyclopentyl;

$R^4$ is H or $C_{1-6}$ alkyl;

$R^5$ is H;

D is a 5 atom saturated alkylene chain; and

A is a carboxylic acid or a pharmaceutically acceptable salt or ester thereof; and optionally, the compound of formula (III) is present in the reaction mixture at a concentration of less than about 0.015 M.

In another particular embodiment, the compounds of formula IA below:

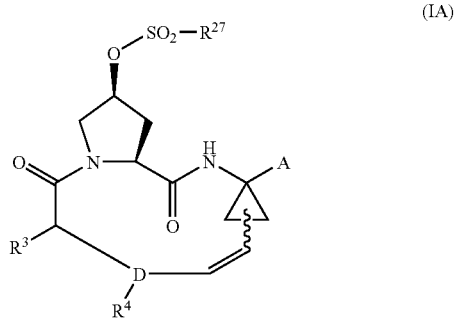

wherein $R^3$, $R^4$, $R^{27}$, A and D have the meaning given above for formula I, may be prepared by macrocyclizing a diene compound of formula IIA:

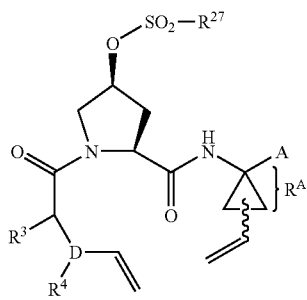

(IIIA)

wherein $R^3$, $R^4$, $R^{27}$, D and A are as defined hereinbefore;
in the presence of a ruthenium catalyst in a suitable organic solvent in a gaseous fluid at supercritical or near-supercritical conditions.

Suitable conditions and catalysts for the metathesis conversion of diene compound IIIA to macrocycle IA include those set forth previously for the metathesis conversion of diene compound III to macrocycle I.

Preparation of Starting Materials

The diene compounds of formula (III) used as a starting materials may be obtained from commercially available materials using the techniques described, for example, in U.S. Pat. No. 6,608,027 B1 and U.S. Application Publication No. 2003/0224977 A1.

The diene compounds of formula (IIA) used as a starting materials may be obtained from commercially available materials using the techniques described in steps (i), (ii) and (iii) below:

Step (i)

This step is directed to a process for preparing a compound of formula (1):

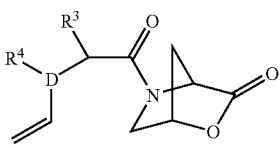

(1)

said process comprising:
reacting a compound of formula (2), or a salt thereof, with a compound of formula (3):

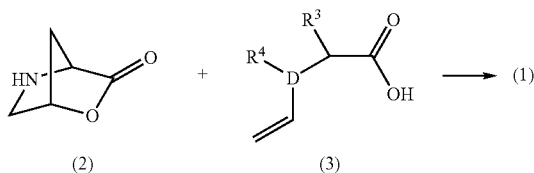

Peptide coupling between compounds of formula (2) and (3) could be obtained under a variety of conditions known in the art using conventional peptide coupling reagents such as DCC, EDC, TBTU, HBTU, HATU, DMTMM, HOBT, or HOAT in aprotic solvents such as dichloromethane, chloroform, DMF, NMP, DMSO.

In a specific embodiment, the compound of formula (2) is used in the form of its mesylate salt.

The cyclic lactone of formula (2), used as starting material can be obtained from a commercially available 4-hydroxyproline compound of formula (4) using standard techniques as outlined in the following general scheme:

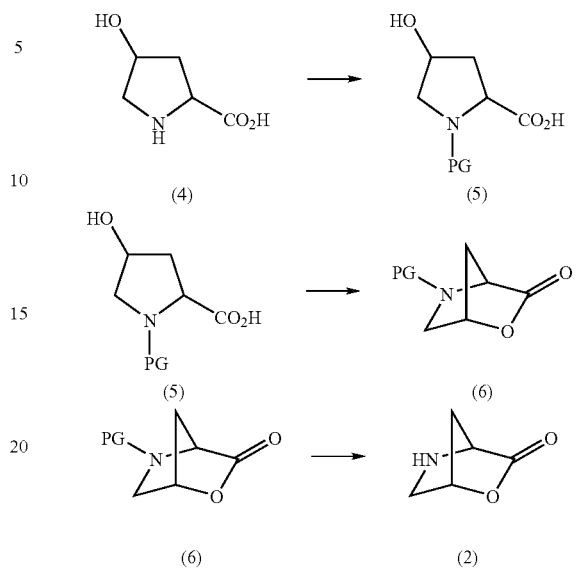

In the first step, an appropriate amino-protecting group is introduced onto the ring nitrogen atom of the 4-hydroxyproline compound of formula (4) using conventional procedures. For example, compound of formula (4) may be dissolved in a suitable solvent and reacted with an appropriate amino-protecting group introducing reagent. For example, and not intending to be limited in its scope, when Boc (tert-butyloxycarbonyl) is the desired protecting group, compound (4) is reacted with the anhydride $Boc_2O$ (or Boc-ON) in a solvent mixture such as Acetone/Water, MIBK/Water, THF/Water to which a base such as NaOH, KOH, LiOH, triethylamine, diisopropylethylamine, or N-methyl-pyrrolidine is added, the reaction being carried out at a temperature between 20–60° C.

In the second step, the protected 4-hydroxyproline compound of formula (5) is converted to the cyclic lactone compound of formula (6) by reaction with an appropriate cyclizing reagent in a suitable solvent. In one embodiment, the OH functionality of the compound of formula (5) is first reacted with an acid chloride (such as methanesulfonyl chloride, p-toluenesulfonyl choride, or trifluoromethanesulfonyl chloride) in a non-protic solvent (such as THF, dioxane, dichloromethane, chloroform, N-methylpyrrolidone, dimethyl sulfoxide, dimethylformamide, acetone, or methylisobutylketone) in the presence of a tertiary amine base (such as N-methyl-pyrrolidine, diisopropylethylamine or triethylamine) to render a compound with a suitable leaving group, followed by cyclization of the obtained compound in a polar non-protic solvent (such as dioxane) in the presence of a tertiary amine base to give the desired cyclic lactone of formula (6).

In the third step, the cyclic lactone compound of formula (6) is deprotected using conventional deprotection techniques, for example, by heating compound of formula (6) in a suitable solvent in the presence of an acid such as p-toluenesulfonic acid, HCl, HBr, HI, HF, $H_2SO_4$, $H_3PO_4$, methanesulfonic acid or trifluoroacetic acid, to obtain the compound of formula (2).

Compound of formula (2) may optionally be converted into a salt form by reaction with an appropriate acid. A specific example of the preparation of the mesylate salt of compound of formula (2) starting from an appropriate 4-hydroxyproline compound of formula (4) is found in the Synthetic Examples section below.

The substituted acid compound of formula (3) used as a starting material may be obtained from commercially available materials using the techniques described in U.S. Pat. No. 6,608,027 B1.

Step (ii)

Step (ii) is directed to a process for preparing a compound of formula (7):

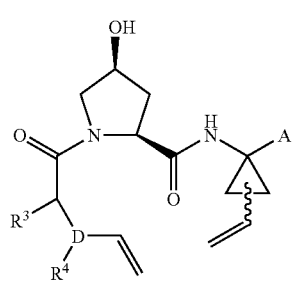

said process comprising:
reacting a compound of formula (1) with a compound of formula (8):

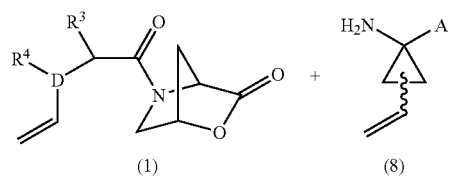

A mixture of compound of formula (1), compound of formula (8) and a suitable base, such as sodium 2-ethylhexanoate (SEH), in a suitable solvent (such as water, toluene, pyridine, a suitable solvent mixture such as toluene/THF or a suitable biphasic solvent system such as water/toluene) is stirred at a temperature from about 20° C. to about 80° C. until completion of the reaction. For work-up the organic layer may be washed and the product isolated after removing the solvent.

The compound of formula (8) used as starting material may be obtained from commercially available materials using the techniques described in International Patent Applications WO 00/09543, WO 00/09558, U.S. Pat. No. 6,323,180 B1 and U.S. Pat. No. 6,608,027 B1.

Step (iii)

Step (iii) is directed to a process for preparing a compound of formula (IIIA):

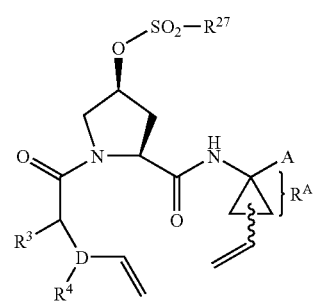

said process comprising:

reacting a compound of formula (7) with a compound of formula (9):

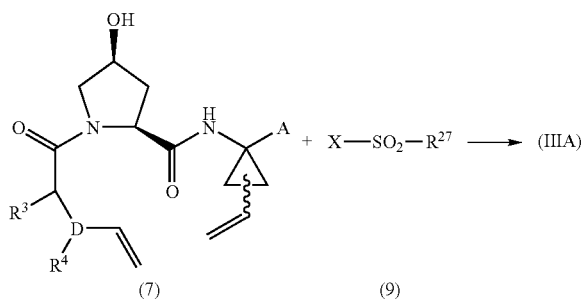

wherein X represents a suitable leaving group and $R^{27}$ is selected from p-tolyl, p-bromophenyl, p-nitrophenyl, methyl, trifluoromethyl, perfluorobutyl and 2,2,2-trifluoroethyl;

To a mixture of compound of formula (7) and an organic base (such as DABCO, triethylamine, 1-methylpyrrolidine or pyridine) in an organic solvent (such as ether, dicholoromethane, cholorform or toluene), a solution of the compound of formula (9) is added and the resultant mixture is stirred at ambient temperature (15–25° C.) until completion of reaction.

The following scheme provides another alternative process using known methods for preparing a diene compound of formula If (a particular formula III compound):

Scheme I

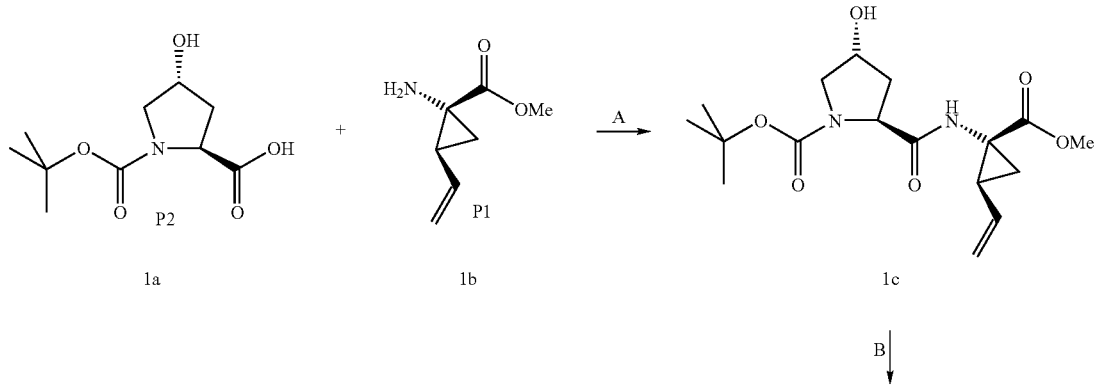

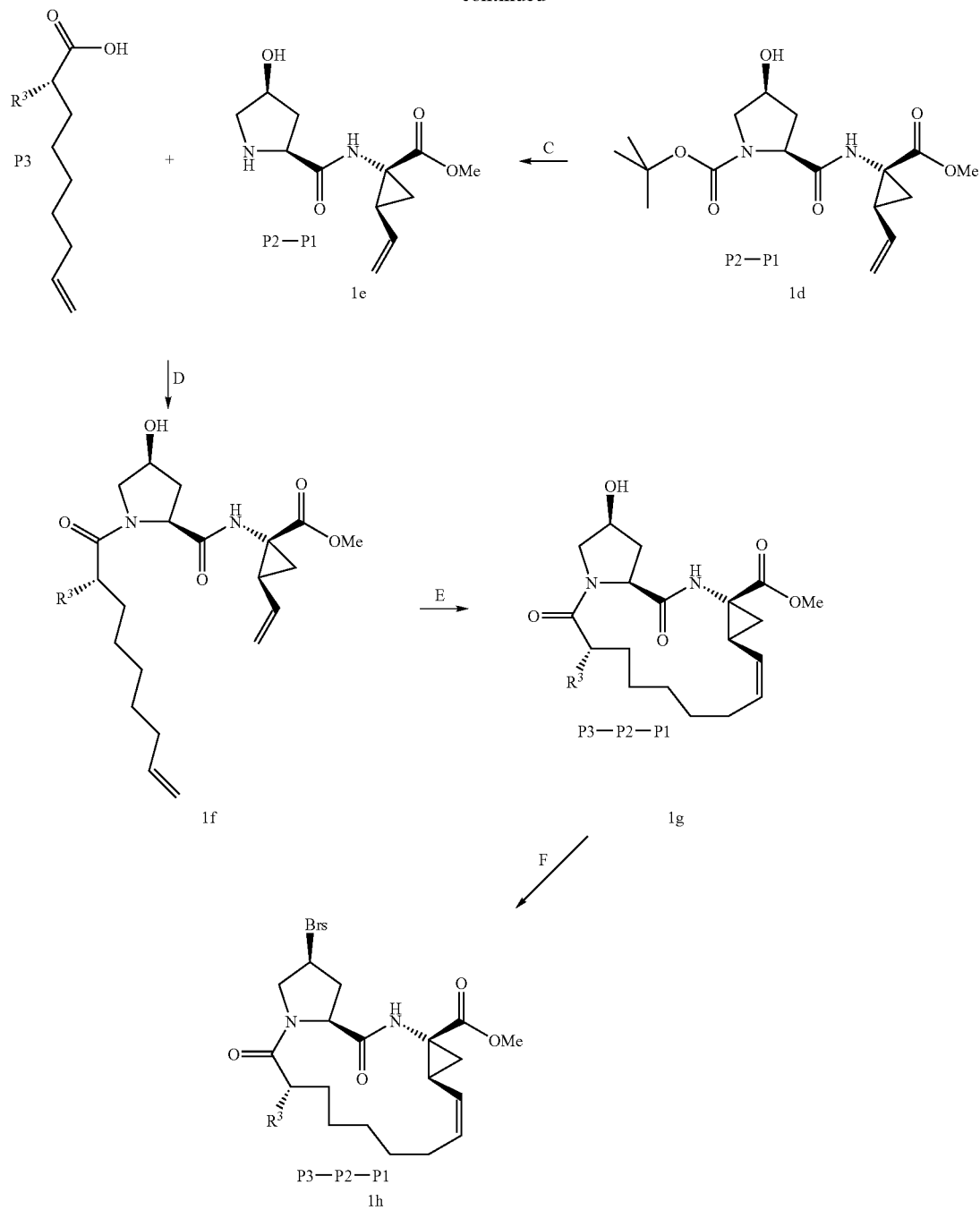

In Scheme I:

Steps A, C, D: Briefly, the P1, P2, and P3 moieties can be linked by well known peptide coupling techniques generally disclosed in WO 00/09543 & WO 00/09558.

Step B: This step involves the inversion of configuration of the 4-hydroxy substituent. There are several ways in which this can be accomplished as will be recognized by persons skilled in the art. One example of a convenient method is the well known Mitsunobu reaction (Mitsunobu Synthesis 1981, January, 1–28; Rano et al. Tet. Lett. 1994, 36, 3779–3792; Krchnak et al. Tet. Lett. 1995, 36, 6193–6196).

Step E: The formation of the macrocycle 1 g from formula 1f can be carried out via an olefin metathesis according to the process of the present invention using a ruthenium-based catalyst such as those set forth previously for the metathesis conversion of diene compound III to macrocycle I.

Step F: Conversion of the hydroxyl group of the proline in 1 g to a suitable leaving group (i.e. brosylate) may be carried out by reacting the free OH with the corresponding halo-derivative (i.e. 4-bromobenzenesulfonyl chloride) to arrive at compound 1 h wherein Brs is a 4-bromobenzene-sulfonyl-oxy group attached to the proline ring.

The following reaction sequence provides yet another alternative method to prepare certain intermediate compounds of formula III (compounds of formula IIIB):

(i) reacting a compound of the formula (II) with a compound of the formula (III) to obtain a compound of the formula (IV):

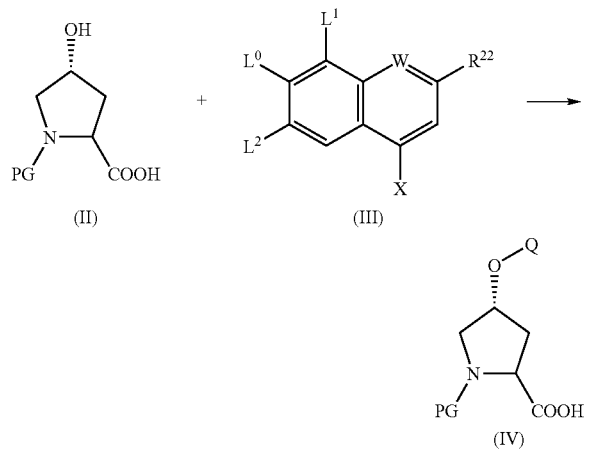

wherein PG is an amino protecting group, X is a halogen atom and Q is a substituent of the following formula:

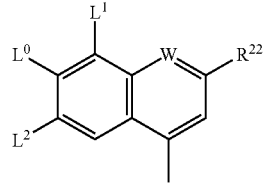

(ii) reacting a compound of the formula (IV) with a compound of the formula (V) to obtain a compound of the formula (VI):

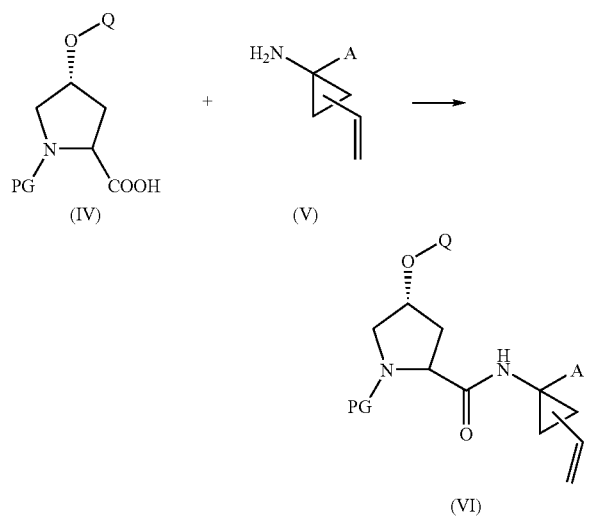

wherein A is an amide of formula —C(O)—NH—$R^{11}$, wherein $R^{11}$ is as defined above for formula I;
or A is a protected carboxylic acid group;

(iii) removing the nitrogen protecting group in the compound of formula (VI) to obtain a compound of the formula (VII):

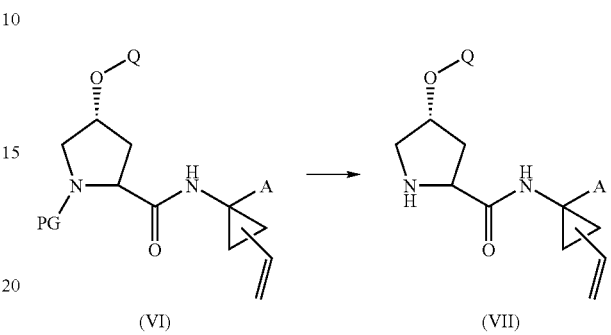

(iv) reacting a compound of the formula (VII) with a compound of the formula (VIII) to obtain a compound of the formula (IIIB):

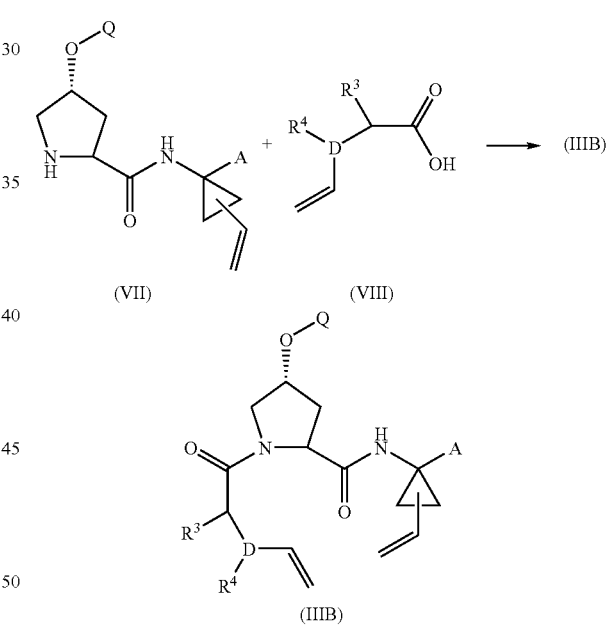

Post RCM Steps

After the RCM reaction leading to the macrocyclic compounds of formula (I), additional reaction steps are possible leading to other compounds of formula (I). For example, when $R^4$ is a leaving group in formula (I), such compounds can be converted to additional compounds of formula (I) wherein $R^4$ is a group of formula (II) by a process comprising: reacting the compound of formula (I) wherein $R^4$ is a leaving group with a compound of formula (IV) to obtain a compound of formula (I) wherein $R^4$ is a group of formula (II):

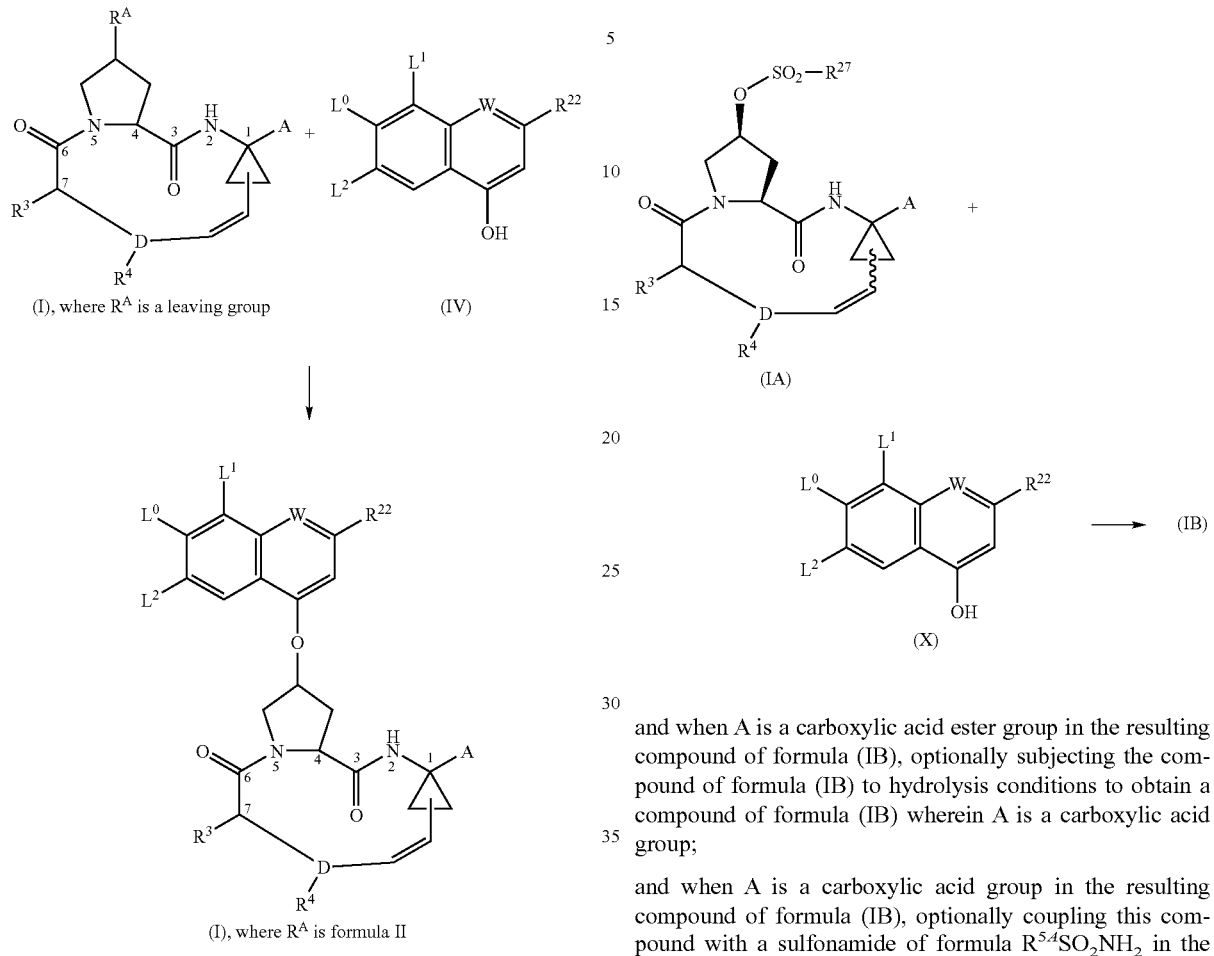

In one embodiment, the cyclized compounds of formula IA above can be used to prepare other compounds of formula I wherein $R^4$ is a group of formula II (i.e. the compounds of formula IB below), using the following sequence:

the process comprising reacting a macrocyclic compound of formula (IA) with a compound of formula (X):

and when A is a carboxylic acid ester group in the resulting compound of formula (IB), optionally subjecting the compound of formula (IB) to hydrolysis conditions to obtain a compound of formula (IB) wherein A is a carboxylic acid group;

and when A is a carboxylic acid group in the resulting compound of formula (IB), optionally coupling this compound with a sulfonamide of formula $R^{54}SO_2NH_2$ in the presence of a suitable coupling agent, such as TBTU or HATU, to obtain a compound of formula (IB) wherein A is —C(O)—NH—$SO_2R^{54}$.

Compounds of formula (IA) and (X) are mixed in a polar non-protic organic solvent (such as THF, Dioxane, dicholormethane, chloroform, N-methylpyrrolidone, dimethyl sulfoxide, dimethylformamide, acetone, or methylisobutylketone) in the presence of an inorganic or organic base (such as cesium carbonate, or DBU) at 40° C. to 100° C. until completion of reaction. Aqueous workup followed by crystallization from a suitable solvent such as ethylacetate-heptane or ethylacetate/methylcyclohexane provides the compounds of formula (IB).

When A is a carboxylic acid ester group in formula (IB), the esterified compound of formula (IB) can optionally be subjected to hydrolysis conditions to obtain the corresponding free carboxylic acid compound. Hydrolysis can be carried out using conventional hydrolysis conditions known in the art. The free carboxylic acid compounds can subsequently be converted to amides or sulfonamides within formula (I) using techniques well known in the art.

The compound of formula (X) used as starting material may be obtained from commercially available materials using the techniques described in International Patent Applications WO 00/09543, WO 00/09558, U.S. Pat. No. 6,323,180 B1 and U.S. Pat. No. 6,608,027 B1.

EXAMPLES

Example 1

Preparation of a Brosylated Diene Intermediate 1

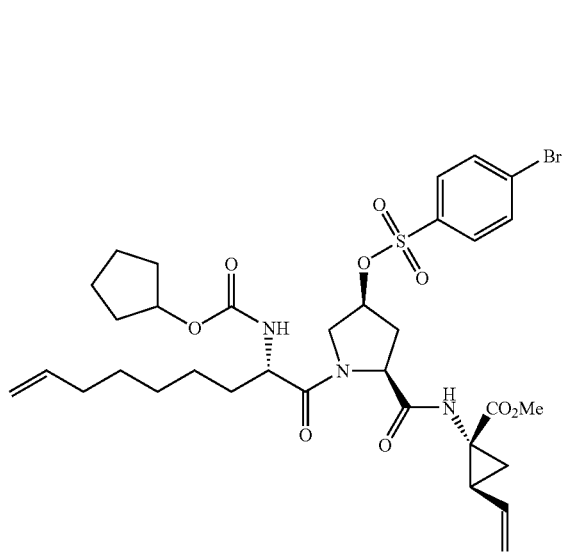

1

Step 1: Introduction of the Boc-protecting Group: Synthesis of (2)

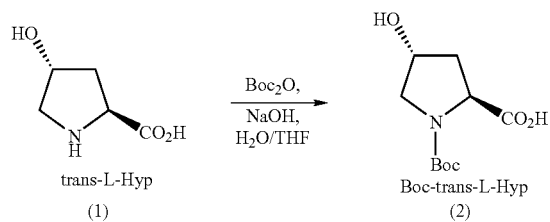

The amino-protection was done with the Boc-protecting-group. (1) (trans-4-hydroxy L-proline) (249.8 g, 1.905 mol) was dissolved in water (375 ml) and 45% sodium hydroxide solution (203 g, 2.286 mol). To ensure good phase transfer, tert-butanol (106 g) was added. In a different procedure, acetone was used instead of THF/tert-butanol. The reaction mixture was heated to 50° C. and the anhydride $Boc_2O$ (424 g, 1.943 mol) was dissolved in THF (425 ml, or acetone) is slowly added. The reaction is exothermic and generates gas ($CO_2$) as the $Boc_2O$ was added. If the reaction does not proceed as wanted, catalytic amounts of DMAP (2.3 g, 19 mmol) can be added. After the addition of the $Boc_2O$, the reaction mixture is kept ½–1 h at 50° C., and the THF was removed by partial distillation. The pH of the remaining solution was adjusted to about pH3 with concentrated HCl (204 g, 2.076 mol) and the product was then extracted with MIBK (1 liter) and again with MIBK (375 ml). The organic layer was heated and some of the solvent was distilled off to remove traces of water. The product was crystallized from this solution by adding MCH (1.25 l), isolated by filtration, washed twice with MCH (375 ml) and dried overnight at 40° C.

Yield: 77–78%, colorless crystals, $F_p$=126–128° C.

Step 2: Formation of the Lactone; Synthesis of (3)

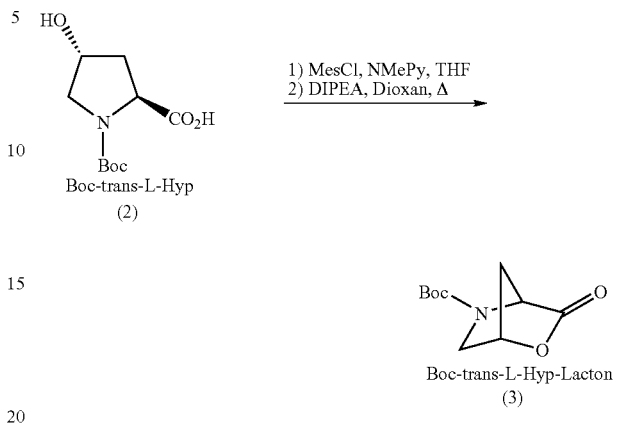

(2) (416.3 g, 1.8 mol) is dissolved in THF (2.08 l) and cooled with ice to a temperature from about −5—to about −10° C. Mesylchloride (392 g, 3.4 mol) and N-Methylpyrrolidine (429 g, 5 mol) is added and the mixture stirred for about 1½ h at about −5° C. The mixture is washed with water and heated up to reflux. Dioxane (2.08 l) is poured in and the THF is distilled off. After cooling down to room temperature, DIPEA (233 g, 1.8 mol) is added and the mixture is heated to reflux. After 1 h part of the solvent (830 ml) is distilled off, cooled to ambient temperature and a $KHSO_4$-solution (14.4 g in 2.08 l water) is poured in and the solution is allowed to cool down to room temperature. The resulting crystals are isolated by filtration, washed with water and dried overnight at 45° C.

Yield: 78–82%, colorless needles, $F_p$=111° C.

Step 3: Deprotection of the Lactone; Synthesis of (4)

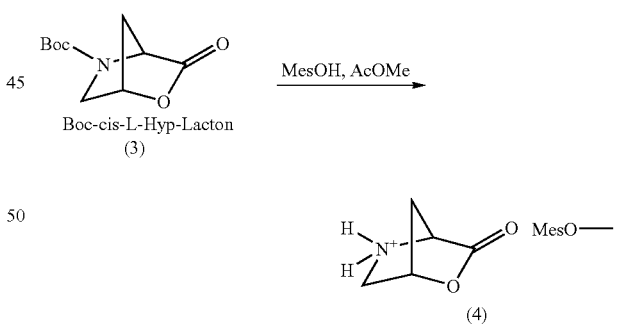

The lactone (3) (267 g, 1.25 mol) is dissolved in Methylisobutylketone (1467 ml). The suspension is heated up to 50° C. until the lactone is completely dissolved and a part of the solvent (130 ml) is distilled off to remove traces of water. Methansulfonic acid (240 g, 2.5 mol) is added slowly to the reaction mixture. During the addition gas is evolved ($CO_2$, Isobutene). The reaction mixture is allowed to cool to room temperature and the resulting crystals are isolated by filtration, washed twice with acetone (each 400 ml) and dried overnight at 40° C.

Yield: 93–98%, colorless crystals, 208–210° C.

Step 4: Coupling with (5): Synthesis of the Dipeptide (6)

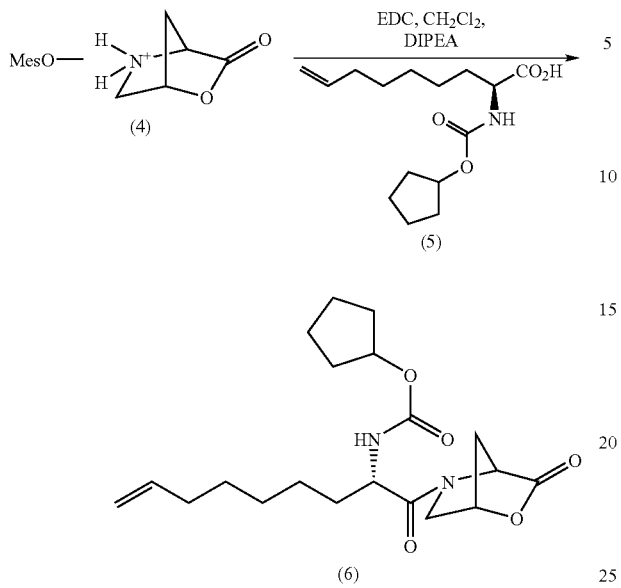

Compound (5) may optionally be obtained by releasing it from a salt form of the compound. For example, if a DCHA salt form is used (5)·DCHA (61.4 g, 132 mmol) is dissolved in toluene (160 ml) and the resulting solution is washed with diluted sulfuric acid (5.3 g in 80 ml water) and water (80 ml). After phase separation, the solution is treated with charcoal and filtered and the resulting solution stored at room temperature.

The deprotected lactone (4) (24.9 g, 119 mmol) and EDC.HCl (26.8 g, 140 mmol) are suspended in dichloromethane (140 ml) and cooled to room temperature. The suspension is treated with the (5)-solution generated before. To this suspension, di-isopropylethylamine (Hünigs-Base, 16.3 g, 130 mmol) is slowly added while the reaction is kept under nitrogen at temperatures below 20° C. The suspension is filtered, and the resulting solution is washed water (80 ml), diluted acetic acid (1.3 g in 80 ml water), 5% sodium bicarbonate solution (80 ml) and again with water (80 ml). After phase separation, dichloromethane is distilled off under reduced pressure. The resulting solution can directly be used for the next step. Otherwise, the product can be isolated by crystallization from MCH.

Yield: 95% (GC), yellowish solution, $F_p$=58–60° C.

Step 5: Synthesis of (8)

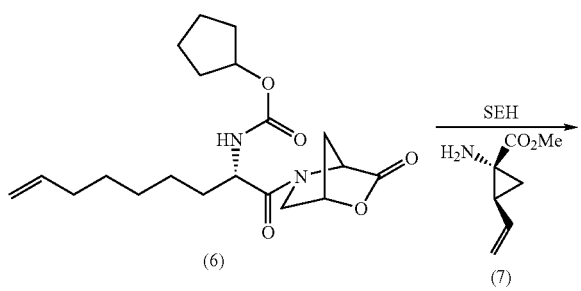

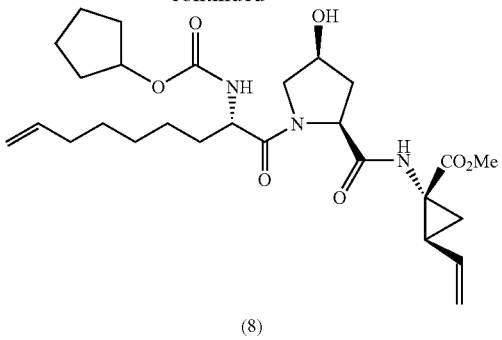

A mixture of (6) (10.0 g, 23.7 mmol, 1.0 eq.), (7) (7.6 g, 24.2 mmol, 1.02 eq.) and sodium 2-ethylhexanoate (SEH) (5.9 g, 35.6 mmol, 1.5 eq.) in water (43 ml) and toluene (12 ml) is stirred at 80° C. for 2 h. For work-up toluene (75 ml) is added at 80° C. After stirring and separation of the aqueous layer, the organic layer is washed with 1M $Na_2CO_3$ (3×30 ml), 0.5M HCl (30 ml) and water (2×30 ml). The solvent is removed under vacuum.

Yield of (8): 11.7 g, 22.5 mmol, 95%; purity: >95% (peak-area HPLC) as a slightly yellow oil.

Step 6. Brosylation of (8); Synthesis of Diene 1

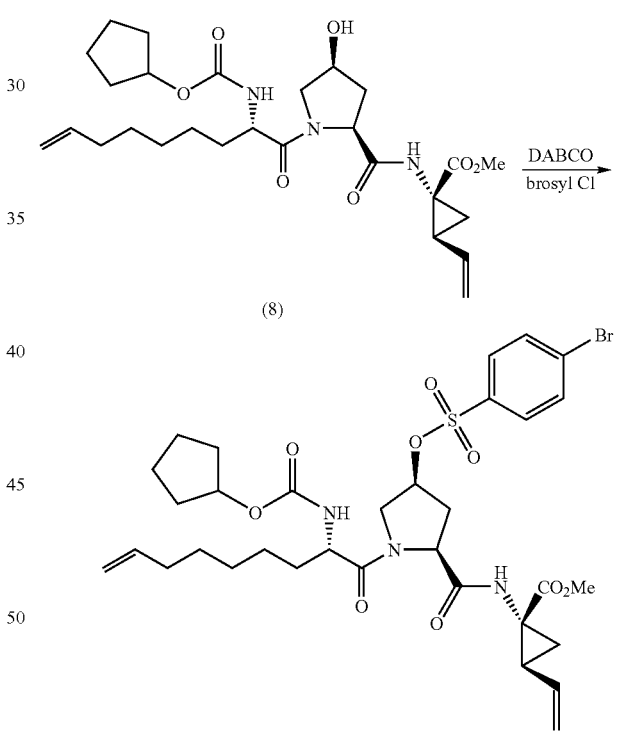

To a mixture of (8) (10.7 g, 18.5 mmol, 1.0 eq.) and DABCO (3.3 g, 29.7 mmol, 1.6 eq.) and toluene (23 ml) a solution of 4-bromobenzenesulfonyl chloride (brosyl chloride, 6.6 g, 26.0 mmol, 1.4 eq.) in toluene (15 ml) is added slowly at room temperature. The mixture is stirred for 2 h. For work-up the organic layer is washed with 1M $Na_2CO_3$ (2×21 ml), diluted with THF (21 ml) and washed with 0.5M HCl (21 ml) and water (2×21 ml). The solvent is removed under vacuum.

Yield of (1): 12.3 g, 16.7 mmol, 90%; purity: >95% (peak-area HPLC) as a slightly orange oil. A charcoal treatment of the crude product is possible.

Step 7: Ring-Closing Metathesis of Diene 1 Under $CO_2$

Catalyst Used:

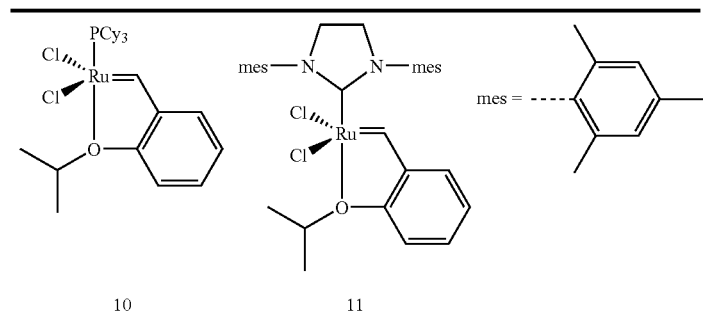

The best conditions so far indicated that the RCM of 1 could take place in ~80% assay yield with ~6% dimers with catalyst 11 (20% loading) in 30 min.

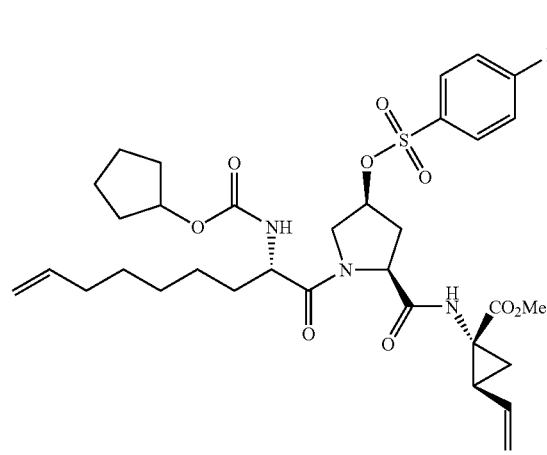

The first fourteen experiments were run on an SFX220 Isco Supercritical Fluid Extractor. A reactor was charged with a glass vial filled with 1 in toluene and the catalyst 10 or 11 was added directly to the reactor (the two compounds are physically apart prior to the pressurization). The chamber was sealed and the system brought to the desired temperature and pressure of $CO_2$. At the end of the experiment, the reactor was vented, and its content poured into a separate vial containing a freshly prepared solution of 4M Trishydroxymethylphosphine (THP) (60 eq). The product was then assayed by HPLC.

For experiment 15: to a 330 mL autoclave was added 8.3 g of 1 (11.2 mmol) in 22 mL toluene. The pressure was raised to 1500 psi and the temperature to 80° C. The system was equilibrated within a few minutes and a solution of 11 (see loading [mol %] in table 1 below) in 34 mL toluene was added within 10 min. The reaction mixture was stirred for 2 h, 1M THP was introduced (60 eq) and temperature and pressure were brought to ambient conditions. The content of the reactor was collected and combined with the rinsing (toluene was used). The resulting solution was assayed by HPLC.

TABLE 1

| | Catalyst | Loading* [mol %] | T [° C.] | P [bar] | t [min] | c [M] | yield | comments |
|---|---|---|---|---|---|---|---|---|
| 1 | 11 | 50 | 50 | 96.5 | 30 | 0.014 | 65% | <5% dimers |
| 2 | 11 | 25 | 50 | 96.5 | 30 | 0.01 | 75% | <5% dimers |
| 3 | 10 | 70 | 50 | 96.5 | 30 | 0.007 | 60% | 12–15% dimers |
| 4 | 10 | 50 | 80 | 345 | 30 | 0.008 | 80% | 8% dimers |
| 5 | 10 | 50 | 70 | 172 | 240 | 0.01 | 85% | 6% dimers |
| 6 | 11 | 5 | 50 | 96.5 | 30 | 0.08 | 15% | 15% dimers |
| 7 | 11 | 10 | 80 | 172 | 30 | 0.5 | 20% | 35% dimers |
| 8 | 11 | 10 | 80 | 345 | 30 | 0.5 | 30% | 35% dimers |
| 9 | 11 | 10 | 80 | 345 | 30 | 1 | 12% | 65% dimers |
| 10 | 11 | 50 | 25 | 345 | 30 | 0.1 | 15% | 15% dimers |
| 11 | 11 | 10 | 70 | 241 | 30 | 0.65 | 17% | 48% dimers |
| 12 | 11 | 10 | 70 | 172 | 30 | 0.5 | 25% | 55% dimers |
| 13 | 11 | 10 | 70 | 241 | 30 | 0.5 | 20% | 40% dimers |
| 14 | 11 | 10 | 80 | 241 | 30 | 0.5 | 31% | 42% dimers |
| 15 | 11 | 20 | 80 | 103 | 180 | 0.2 | 18% | 75% conversion |

*1 = Catalyst loading in mol % according to 1.

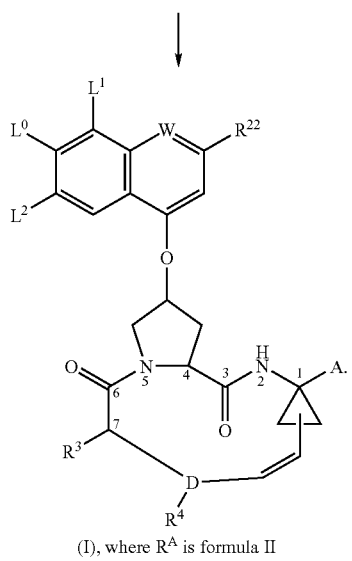

The invention claimed is:

1. A process for preparing a compound of the following formula I, said process comprising cyclizing a compound of the following formula III in the presence of a ruthenium catalyst in a suitable organic solvent, wherein the process is performed in a gaseous fluid at supercritical or near-supercritical conditions to obtain a compound of the following formula I:

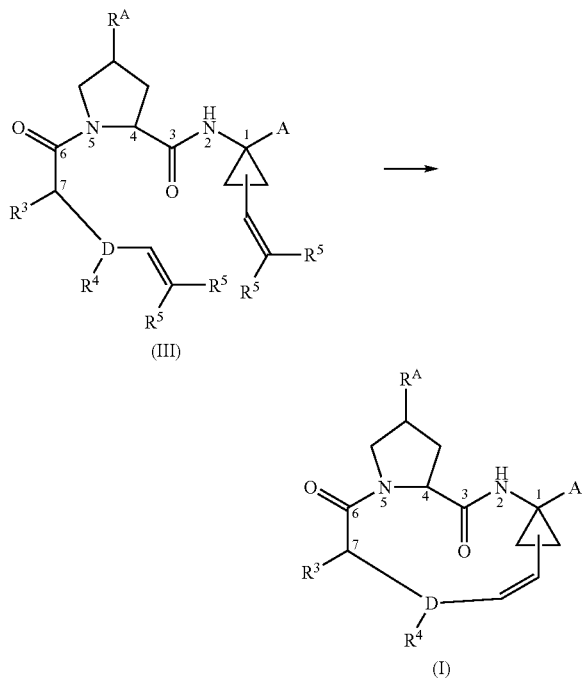

wherein
$R^A$ is a leaving group or a group of formula II

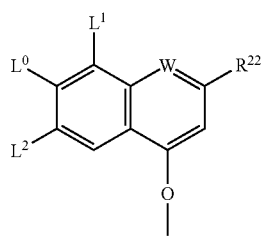

W is CH or N,
$L^0$ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^{23})_2$, wherein each $R^{23}$ is independently H, $C_{1-6}$ alkyl or $C_{3-6}$ cycloalkyl;
$L^1$, $L^2$ are each independently H, halogen, $C_{1-4}$alkyl, —O—$C_{1-4}$alkyl, or —S—$C_{1-4}$alkyl (the sulfur being in any oxidized state); or
$L^0$ and $L^1$ or
$L^0$ and $L^2$ may be covalently bonded to form together with the two C-atoms to which they are linked a 4-, 5- or 6-membered carbocyclic ring wherein one or two (in the case of a 5- or 6-membered ring)-CH$_2$— groups not being directly bonded to each other, may be replaced each independently by —O— or NR$^a$ wherein R$^a$ is H or $C_{1-4}$alkyl, and wherein said ring is optionally mono- or di-substituted with $C_{1-4}$ alkyl;
$R^{22}$ is H, halo, C$_{-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxyalkyl, $C_{3-6}$cycloalkyl, $C_{6\ or\ 10}$ aryl or Het, wherein Het is a five-, six-, or seven-membered saturated or unsaturated heterocycle containing from one to four heteroatoms selected from nitrogen, oxygen and sulfur;
said cycloalkyl, aryl or Het being substituted with $R^{24}$, wherein $R^{24}$ is H, halo, $C_{1-6}$ alkyl, $C_{3-6}$ cycloalkyl, $C_{1-6}$ alkoxy, $C_{3-6}$ cycloalkoxy, NO$_2$, $N(R^{25})_2$, NH—C(O)—$R^{25}$; or NH—C(O)—NH—$R^{25}$, wherein each $R^{25}$ is independently: H, $C_{1-6}$ alkyl or $C_{3-6}$ cycloalkyl;
or $R^{24}$ is NH—C(O)—OR$^{26}$ wherein $R^{26}$ is $C_{1-6}$ alkyl or $C_{3-6}$ cycloalkyl;
$R^3$ is hydroxy, NH$_2$, or a group of formula —NH—$R^9$, wherein $R^9$ is $C_{6\ or\ 10}$ aryl, heteroaryl, —C(O)—$R^{20}$, —C(O)—NHR$^{20}$ or —(O)—OR$^{20}$, wherein $R^{20}$ is $C_{1-6}$ alkyl or $C_{3-6}$ cycloalkyl;
D is a 3 to 7 atom saturated alkylene chain optionally containing one to three heteroatoms independently selected from: O, S or N—$R^{27}$, wherein $R^{27}$ is H, $C_{1-6}$alkyl, $C_{3-6}$cycloalkyl or C(O)$R^{28}$, wherein $R^{28}$ is $C_{1-6}$alkyl, $C_{3-6}$cycloalkyl or $C_{6\ or\ 10}$ aryl;
$R^4$ is H, or from one to three substituents at any carbon atom of said chain D, said substituent independently selected from the group consisting of: $C_{1-6}$ alkyl, $C_{1-6}$ haloalkyl, $C_{1-6}$ alkoxy, hydroxy, halo, amino, oxo, thio, or $C_{1-6}$ thioalkyl;
A is an amide of formula —C(O)—NH—$R^{11}$, wherein $R^{11}$ is selected from the group consisting of: $C_{1-8}$ alkyl, $C_{3-6}$ cycloalkyl, $C_{6\ or\ 10}$ aryl, $C_{7-16}$ aralkyl, or SO$_2$R$^{54}$ wherein $R^{54}$ is $C_{1-8}$ alkyl, $C_{3-7}$ cycloalkyl,$C_{1-6}$ alkyl-$C_{3-7}$ cycloalkyl;
or A is a carboxylic acid or a pharmaceutically acceptable salt or ester thereof.

2. A process according to claim 1, wherein the gaseous fluid is selected from carbon dioxide, nitrous oxide, trifluoromethane, ethane, ethylene, propane, sulfur hexafluoride, propylene, butane, isobutane, pentane, and mixtures thereof.

3. A process according to claim 1, wherein the gaseous fluid is carbon dioxide.

4. A process according to claim 1, wherein the process is performed at a temperature in the range of about 0.8 to 3.0 times the critical temperature of the gaseous fluid in degrees Kelvin.

5. A process according to claim 1, wherein the process is performed at a temperature in the range of about 2.0 to 3.0 times the critical temperature of the gaseous fluid in degrees Kelvin.

6. A process according to claim 1, wherein the process is performed at a pressure in the range of about 0.5 to 30 times the critical pressure of the gaseous fluid.

7. A process according to claim 1, wherein the process is performed at a pressure in the range of about 1 to 10 times the critical pressure of the gaseous fluid.

8. A process according to claim 1, wherein the gaseous fluid is carbon dioxide, and the process is performed at a temperature in the range of about 70 to 80° C. and a pressure in the range of about 95 to 238 bar.

9. A process according to claim 1, wherein the ruthenium catalyst is selected from:

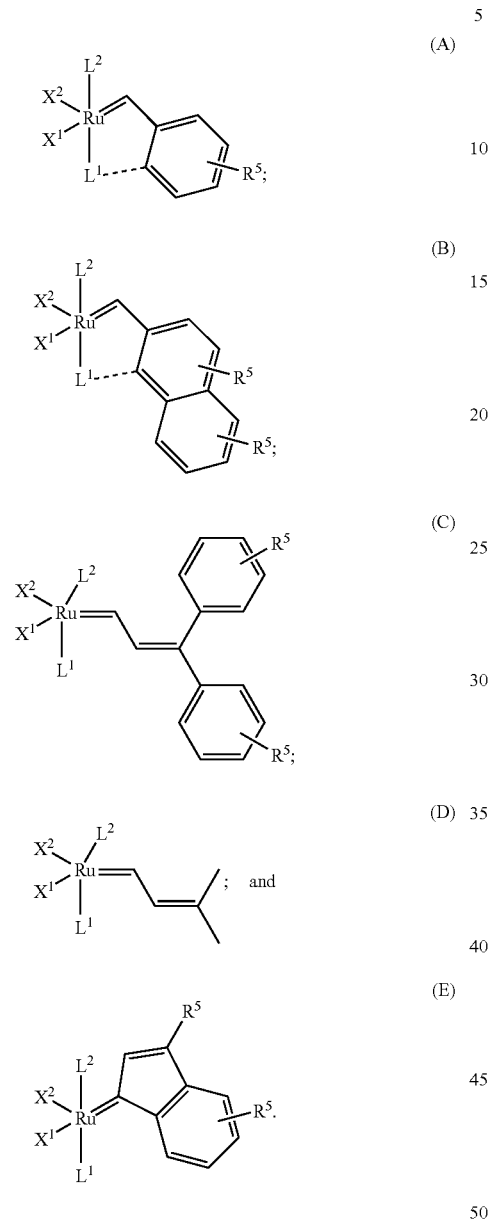

wherein
- $X^1$ and $X^2$ each independently represent an anionic ligand,
- $L^1$ represents a neutral electron donor ligand which is bonded to the ruthenium atom and is optionally bonded to the phenyl group, and
- $L^2$ represents a neutral electron donor ligand which is bonded to the ruthenium atom;
- and $R^5$ is selected from one or more substituents on the benzene ring, each substituent independently selected from hydrogen, $C_{1-6}$alkyl, halo$C_{1-6}$alkyl, HS—$C_{1-6}$alkyl, HO—$C_{1-6}$alkyl, perfluoro$C_{1-6}$alkyl, $C_{3-6}$ cycloalkyl, $C_{1-6}$alkoxy, hydroxyl, halogen, nitro, imino, oxo, thio or aryl; and
- wherein $X^2$ and $L^2$ may optionally together form a chelating bidentate ligand.

10. A process according to claim 9, wherein the ruthenium catalyst is selected from:

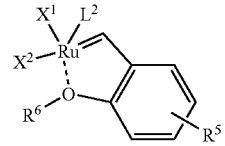

(A-1)

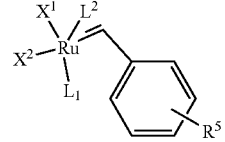

(A-2)

wherein:
- $L^1$ is a trisubstituted phosphine group of the formula $PR_3$, wherein R is selected from $C_{1-6}$alkyl and $C_{3-8}$cycloalkyl,
- $L^2$ is a trisubstituted phosphine group of the formula $PR_3$, wherein R is selected from $C_{1-6}$alkyl and $C_{3-8}$cycloalkyl,
- or $L^2$ is a group of the formula A or B:

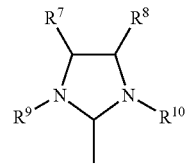

(A)

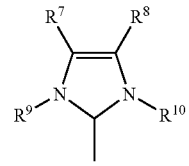

(B)

wherein
- $R^7$ and $R^8$ each independently represent a hydrogen atom or a $C_{1-6}$ alkyl, $C_{2-6}$ alkenyl, $C_{6-12}$ aryl or $C_{6-12}$ aryl-$C_{1-6}$ alkyl group; and
- $R^9$ and $R^{10}$ each independently represent a hydrogen atom or a $C_{1-6}$ alkyl, $C_{2-6}$ alkenyl, $C_{6-12}$ aryl or $C_{6-12}$ aryl-$C_{1-6}$ alkyl group, each optionally substituted by one, two or three groups selected from hydrogen, $C_{1-6}$alkyl, halo$C_{1-6}$alkyl, HS—$C_{1-6}$alkyl, HO—$C_{1-6}$alkyl, perfluoro$C_{1-6}$alkyl, $C_{3-6}$ cycloalkyl, $C_{1-6}$alkoxy, hydroxyl, halogen, nitro, imino, oxo, thio or aryl;
- $X^1$ and $X^2$ each independently represent a halogen atom;
- $R^5$ represent hydrogen or nitro; and
- $R^6$ represents a $C_{1-6}$ alkyl group.

11. A process according to claim 10, wherein the ruthenium catalyst is selected from:

[chemical structures of ruthenium catalysts]

where Ph is phenyl and Mes is 2,4,6-trimethylphenyl.

12. A process according to claim 1, wherein in the compounds of formula (I):
- $R^A$ is a leaving group selected from: OH, O—PG, where PG is a protecting group, or —$OSO_2$—$R^{27}$, wherein $R^{27}$ is selected from p-tolyl, p-bromophenyl, p-nitrophenyl, methyl, trifluoromethyl, perfluorobutyl and 2,2,2-trifluoroethyl;
- or $R^A$ is a group of formula II, and
- W is N;
- $L^0$ is H, $C_{1-6}$ alkyl, $C_{1-6}$ alkoxy, hydroxy, chloro;
- $L^1$ and $L^2$ are each independently H, halogen or $C_{1-4}$ alkyl;
- $R^{22}$ is H, $C_{1-6}$ thioalkyl, $C_{1-6}$ alkoxy, phenyl or Het selected from the group consisting of:

[heterocyclic structures with $R^{24}$ substituents]

wherein $R^{24}$ is H, $C_{1-6}$ alkyl, NH—$R^{25}$, NH—C(O)—$R^{25}$; NH—C(O)—NH—$R^{25}$,
wherein each $R^{25}$ is independently: H, $C_{1-6}$ alkyl, or $C_{3-6}$ cycloalkyl;
or NR—C(O)—$OR^{26}$, wherein $R^{26}$ is $C_{1-6}$ alkyl; or $R^3$ is NR—C(O)—$OR^{20}$, wherein $R^{20}$ is $C_{1-6}$ alkyl, or $C_{3-6}$ cycloalkyl;

D is a 4 to 6 atom saturated alkylene chain optionally containing one or two heteroatoms independently selected from: O, S or N—$R^{27}$, wherein $R^{27}$ is H, $C_{1-6}$ alkyl or $C_{2-7}$ acyl;

$R^4$ is H or $C_{1-6}$ alkyl;

and A is a carboxylic acid or a pharmaceutically acceptable salt or ester thereof.

13. A process according to claim 1, wherein in the compounds of formula (I):
- $R^A$ is a leaving group selected from: OH and —$OSO_2$—$R^{27}$, wherein $R^{27}$ is selected from p-tolyl, p-bromophenyl, p-nitrophenyl, methyl, trifluoromethyl, perfluorobutyl and 2,2,2-trifluoroethyl;
- $R^3$ is NH—C(O)—$OR^{20}$, wherein $R^{20}$ is butyl, cyclobutyl or cyclopentyl;
- $R^4$ is H or $C_{1-6}$ alkyl;
- D is a 5 atom saturated alkylene chain; and
- A is a carboxylic acid or a pharmaceutically acceptable salt or ester thereof.

14. A process according to claim 1, wherein in the compounds of formulas (I) and (III):
- $R^A$ is —$OSO_2$—$R^{27}$, wherein $R^{27}$ is p-bromophenyl;
- $R^3$ is NH—C(O)—$OR^{20}$, wherein $R^{20}$ is cyclopentyl;
- $R^4$ is H;
- D is a 5 atom all carbon chain containing one cis double bond at position 13,14; and the right-hand portion of formula (I) is a moiety of the following formula wherein the position 14-cyclopropyl bond is syn to the ester group:

[chemical structure showing cyclopropane with COOMe, amide NH, and cis double bond at positions 13,14]

15. A process according to claim 1, wherein the compound of formula III is present in the reaction mixture at a concentration of about 0.007 M to 0.014 M and the catalyst is present in the reaction mixture at a concentration of about 25 to 50 mol % relative to the compound of formula III.

16. A process according to claim 1, wherein:
(a) the gaseous fluid is carbon dioxide and the process is performed at a temperature in the range of about 70 to 80° C. and a pressure in the range of about 95 to 238 bar;

(b) the ruthenium catalyst is selected from:

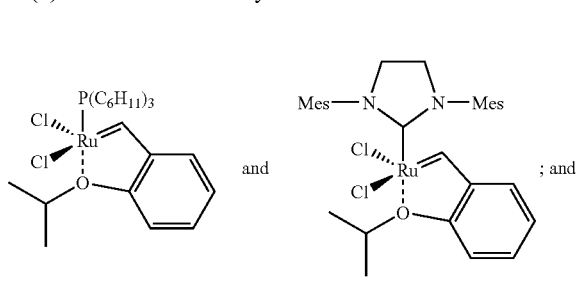

and

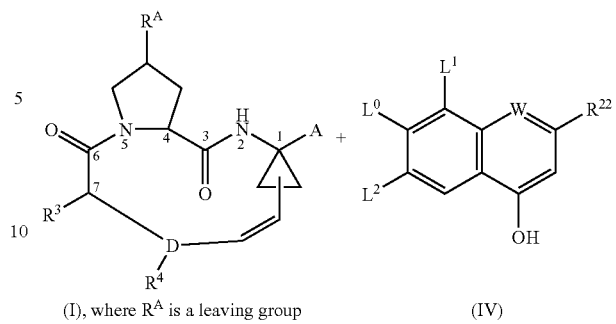

; and (c) in the compounds of formula (I) and (III):
$R^4$ is a leaving group selected from: OH and —$OSO_2$—$R^{27}$, wherein $R^{27}$ is selected from p-tolyl, p-bromophenyl, p-nitrophenyl, methyl, trifluoromethyl, perfluorobutyl and 2,2,2-trifluoroethyl;
$R^3$ is NH—C(O)—$OR^{20}$, wherein $R^{20}$ is butyl, cyclobutyl or cyclopentyl;
$R^4$ is H or $C_{1-6}$ alkyl;
$R^5$ is H;
D is a 5 atom saturated alkylene chain; and
A is a carboxylic acid or a pharmaceutically acceptable salt or ester thereof.

17. A process according to claim 16, wherein the compound of formula III is present in the reaction mixture at a concentration of about 0.007 M to 0.014 M and the catalyst is present in the reaction mixture at a concentration of about 25 to 50 mol % relative to the compound of formula III.

18. A process according to claim 1, wherein when $R^A$ is a leaving group, further comprising reacting the compound of formula (I) wherein $R^A$ is a leaving group with a compound of formula (IV) to obtain a compound of formula (I) wherein $R^A$ is a group of formula (II), wherein $R^3$, $R^4$, D, A, $L^0$, $L^1$, $L^2$, W, $R^{22}$ are as defined in claim 1: